(12) United States Patent
Li (10) Patent No.: US 9,670,029 B2
(45) Date of Patent: Jun. 6, 2017

(54) STRIP-SHAPED WIRE STORING AND TRANSFERRING DEVICE

(71) Applicant: TRIMAX TECHNOLOGY DEVELOPMENT (SHENZHEN) CO. LTD., Shenzhen (CN)

(72) Inventor: Shusum Li, Shenzhen (CN)

(73) Assignee: TRIMAX TECHNOLOGY DEVELOPMENT (SHENZHEN) CO. LTD., Shenzhen (CN)

( * ) Notice: Subject to any disclaimer, the term of this patent is extended or adjusted under 35 U.S.C. 154(b) by 369 days.

(21) Appl. No.: 14/064,816

(22) Filed: Oct. 28, 2013

(65) Prior Publication Data

US 2014/0048643 A1 Feb. 20, 2014

Related U.S. Application Data

(63) Continuation of application No. PCT/CN2012/073441, filed on Mar. 31, 2012.

(30) Foreign Application Priority Data

Apr. 26, 2011 (CN) .......................... 2011 1 0105508

(51) Int. Cl.
*B65H 49/34* (2006.01)
*B65H 49/20* (2006.01)
(Continued)

(52) U.S. Cl.
CPC ..... *B65H 49/205* (2013.01); *A61B 17/06133* (2013.01); *B65H 49/34* (2013.01);
(Continued)

(58) Field of Classification Search
CPC .. B65H 49/205; B65H 49/34; B65H 2701/36; A61B 17/06133; A61B 2017/06142; A61C 15/043
See application file for complete search history.

(56) References Cited

U.S. PATENT DOCUMENTS 4,232,688 A 11/1980 Day
4,640,167 A 2/1987 Stusack et al.
(Continued)

FOREIGN PATENT DOCUMENTS

CN 2320217 5/1999
CN 102266243 12/2011
(Continued)

*Primary Examiner* — William A Rivera
(74) *Attorney, Agent, or Firm* — Hamre, Schumann, Mueller & Larson, P.C.

(57) ABSTRACT

A strip-shaped wire storing and transferring device is provided. The device includes a driving mechanism covered by a case, a wire cutting mechanism, and a bobbin winder. Wherein, the case includes an upper case and a lower case. The upper case and the lower case are matched and capable of buckling together. The case includes a rectangle portion, a bulge portion, a position portion, a position pole, and an incoming line groove and an outgoing line groove connected by a recess groove. The driving mechanism includes a pressure pole, a main gear strung by a main axle and resisted by a second elastic element, a rotating wheel engaging with the main gear, and a rolling wheel clamped by the rotating wheel and a anti-reverse-rotation device. The wire cutting mechanism includes a cutter shelf and a cutter. The bobbin winder includes a center hole and a bobbin slot.

12 Claims, 7 Drawing Sheets

(51) Int. Cl.
 *A61B 17/06* (2006.01)
 *A61C 15/04* (2006.01)
(52) U.S. Cl.
 CPC ... *A61B 2017/06142* (2013.01); *A61C 15/043* (2013.01); *B65H 2701/36* (2013.01)

(56) References Cited

U.S. PATENT DOCUMENTS

| | | | |
|---|---|---|---|
| 5,280,741 A | | 1/1994 | Bell et al. |
| 5,490,722 A | | 2/1996 | Sonnett et al. |
| D395,950 S | | 7/1998 | Friedman |
| 7,350,768 B1 * | | 4/2008 | Chang ............... B25B 25/00 24/70 ST |
| 8,721,240 B1 * | | 5/2014 | Wu ................. B60P 7/083 410/121 |
| 2010/0006119 A1 | | 1/2010 | Veras et al. |
| 2011/0041300 A1 * | | 2/2011 | Lu ................... B60P 7/083 24/68 CD |

FOREIGN PATENT DOCUMENTS

| | | |
|---|---|---|
| CN | 202069619 | 12/2011 |
| DE | 9307003 | 8/1993 |
| EP | 0643949 | 3/1995 |

\* cited by examiner

STRIP-SHAPED WIRE STORING AND TRANSFERRING DEVICE

TECHNICAL FIELD

The present art and invention relates to a storing and dispensing device for strip-shaped, wire-shaped materials, and more particularly, to a strip, wire or cord storing and dispensing device fit for human engineering mechanics, namely more naturally operated by one hand, with lighter work load, and reduce level of fatigue over an extended time and continuous repeated operation.

BACKGROUND

Currently, the strip, wire or cord type materials used in a medical field, stationery, and general commodity are widely known, but the dispensing devices for integrally managing the storage, dispensing, convenient use, contamination avoidance, and the consumable materials used in wire fetching and using process cannot not be found in the market.

By comparing the prior art disclosed in U.S. Pat. Nos. 5,280,741, 4,232,688, D395950 to this invention, all prior arts and inventions fail to address the following issues:

1. In the prior arts, two hands are required to operate, thereby distracting the focus of the operator after a long time operation;

2. In the prior arts, the length of the material dispensed each time is not equal and no quantization standard as materials to be pulled out manually;

3. Prior arts would make the operator feel fatigue over repeat operations, in terms of the human engineering mechanics perspective;

4. Prior arts did not address the contamination issue, as the wire is easy to be contaminated, polluted due to the wire is exposed outside during a wire fetching operation and wire cutting operation.

SUMMARY

The object of the present invention is for providing strip-shaped, wire-shaped materials storing and dispensing device for solving the problems described above.

For solving the described technical problems, the object of the present invention is realized by following technology schemes.

A strip-shaped, wire-shaped materials storing and dispensing device, comprising a driving mechanism covered by an external casing a cutting mechanism, and a bobbin winder, wherein:

the casing comprises an upper case and a lower case, the upper case and the lower case are matched and are capable of buckling together, the case comprises a rectangle portion, a bulge portion, a position portion, a position pole, and an incoming line groove and an outgoing line groove connected by a recess groove;

the driving mechanism includes a pressure pole, a main gear strung by a main axle and resisted by a second elastic element, a rotating wheel engaging with the main gear, and a rolling wheel clamped by the rotating wheel and a anti-reverse-rotation device;

the wire cutting mechanism comprises a cutter shelf and cutters, and the bobbin winder includes a center hole and a bobbin slot.

Further, the rectangle portion comprises a recess portion capable of sticking a resisting portion of the pressure pole and a first elastic element, a recess opening is arranged opposite to an outlet of the recess portion and the top of the bulge portion.

Further, the position portion includes a position hole and a reverse teeth.

Further, the recess groove defines a clamping portion along a longer inner sidewall and a fixing portion extending from the clamping portion.

Further, the recess groove and the outgoing line groove are disposed on a single wall, the wall defines a crack that interconnects with the recess groove and the outgoing line groove, the outgoing line groove further interconnects with the outgoing line groove.

Further, the pressure pole comprises a main pole portion connected by a pressure cap and a resisting portion, and further comprises a first sawtooth portion defined on one side of the main pole portion.

Further, the main gear comprises a second sawtooth portion and a third sawtooth portion defined on the bottom surface of the main gear.

Further, the rolling wheel clamped by the rotating wheel and the anti-reverse-rotation device, the bottom of the rotating wheel defines a rotating axle, an access point defined on the rotating axle.

Further, the anti-reverse-rotation device comprises bulge points and a stopping portion.

Further, the cutter shelf comprises a button and a holding portion, the cutters are fixed on the inner side of the buttons, the buttons are placed in the recess groove.

Further, the inlet of the incoming line groove and the outlet of the outgoing line groove are inverted awl shaped, the cutting position of the cutter on the top of the inverted awl shaped outlet of the outgoing line groove.

The device further comprises an elastic pole surrounds the position pole, the position pole passes through the center hole of the bobbin winder and the elastic pole is clamped between the inner surface of the center hole and the position pole.

Further, the side of the case defines a watch window, the watch window corresponds to the bobbin winder.

Further, the device further comprising a block fixed between the upper case and the lower case, wherein the block corresponds to the outgoing line groove, the back of the block defines a metal board, the cutter cuts the strip-shaped wire from the front of the block by coordinating with the metal board.

Further, the cutter shelf comprises buttons and a clamping arm bending and extending towards the main axle from one end of the button, the clamping arm is capable of clamping to the main gear to limit the rotation of the main gear.

Further, a pivot connection portion is set between the clamping arm and the end of the button, the clamping arm comprises a first straight section connected to the pivot connection portion, a second straight section connected to a free end of the first straight section, and a hook defined on an end of the second straight section, the hook is capable of hooking the main gear.

As stated above, comparing with the prior art and known techniques, the present invention has the following advantages:

1. Improved Fit, in terms of human engineering mechanics, more naturally operated by hand, more lighter work load, and not easy to feel fatigue;

2. Fitting for the strip-shaped wire with different hardness, different elasticity, different size and different material type.

3. The position where the wire is cut is an inverted conical shaped space, thus the strip-shaped wire is not easy to be jammed or blocked;

4. only one hand is needed to cut and fetch the strip-shaped wire, thereby, the attention of the operator is not easy to be distracted, namely, one hand operation lightens the work load and avoids fatigue resulted by long time operation, allowing greater focus for the operator.

The length of the fetched wire is standardized with each dispensing action, and is correctly quantized to avoid wire waste.

The strip-shaped wire within the container is kept from the external contamination, to be kept sterile, thus avoids the strip-shaped wire exposes outside to be polluted.

It is convenient to fetch and cut the strip-shaped wire and wire is quantized to prevent waste.

DETAILED DESCRIPTION OF THE PREFERRED EMBODIMENTS

Embodiments of the present invention will be explained below in detail with reference to the accompanying drawings. It should be understood that the embodiments described below are only used to explain the present invention, and not intend to limit the present invention.

Referring to FIG. 1 to FIG. 5, the first preferred embodiment of the present invention provides a strip-shaped wire storing and transferring device 100 (hereinafter "device 100"). The strip-shaped wire referred herein includes line-shaped wire. The device 100 includes a driving mechanism 20 covered by a case 10, a wire cutting mechanism 30, and a bobbin winder 40.

Figure 1:
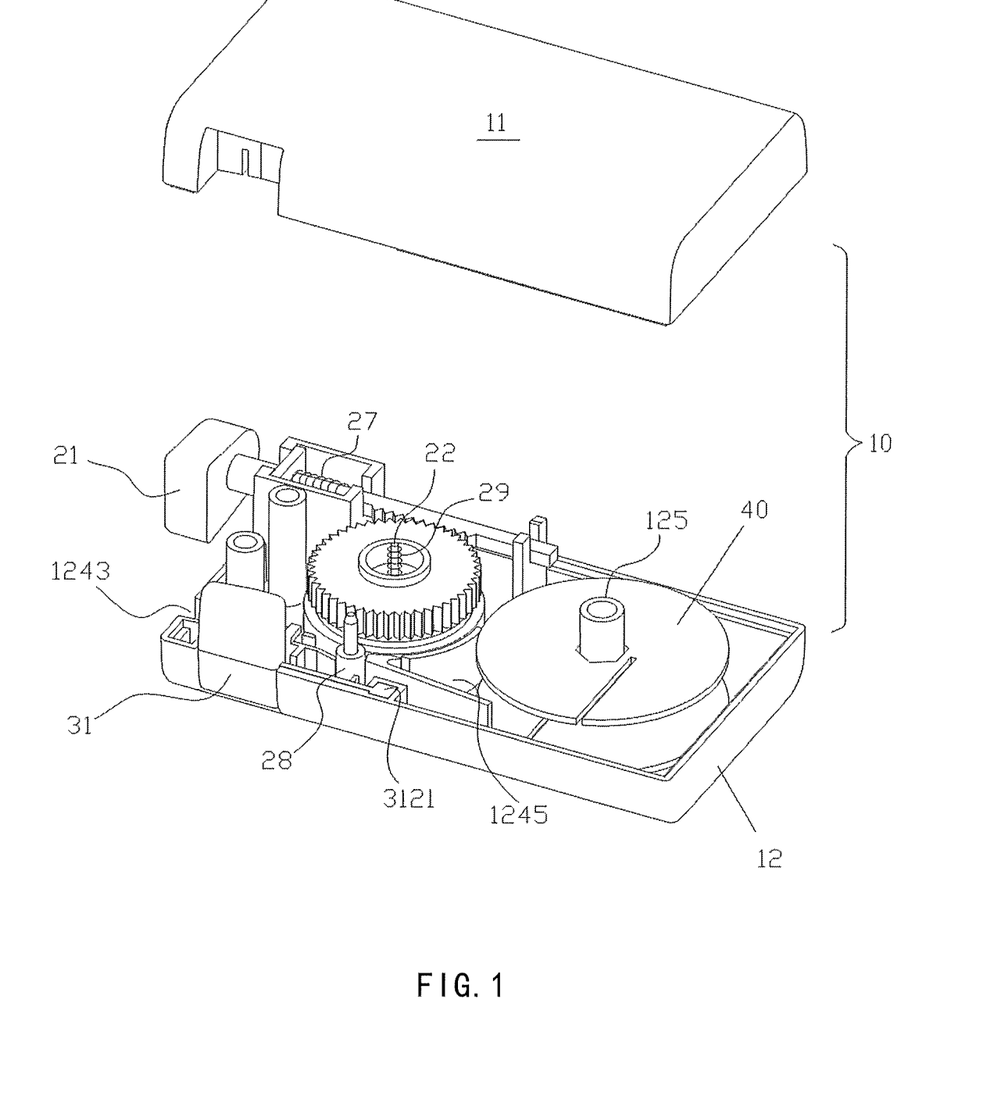
FIG. 1 is an exploded view of a strip-shaped storing and transferring device in accordance with a first preferred embodiment of the present invention.

The case 10 includes an upper case 11 and a lower case 12.

Figure 2:
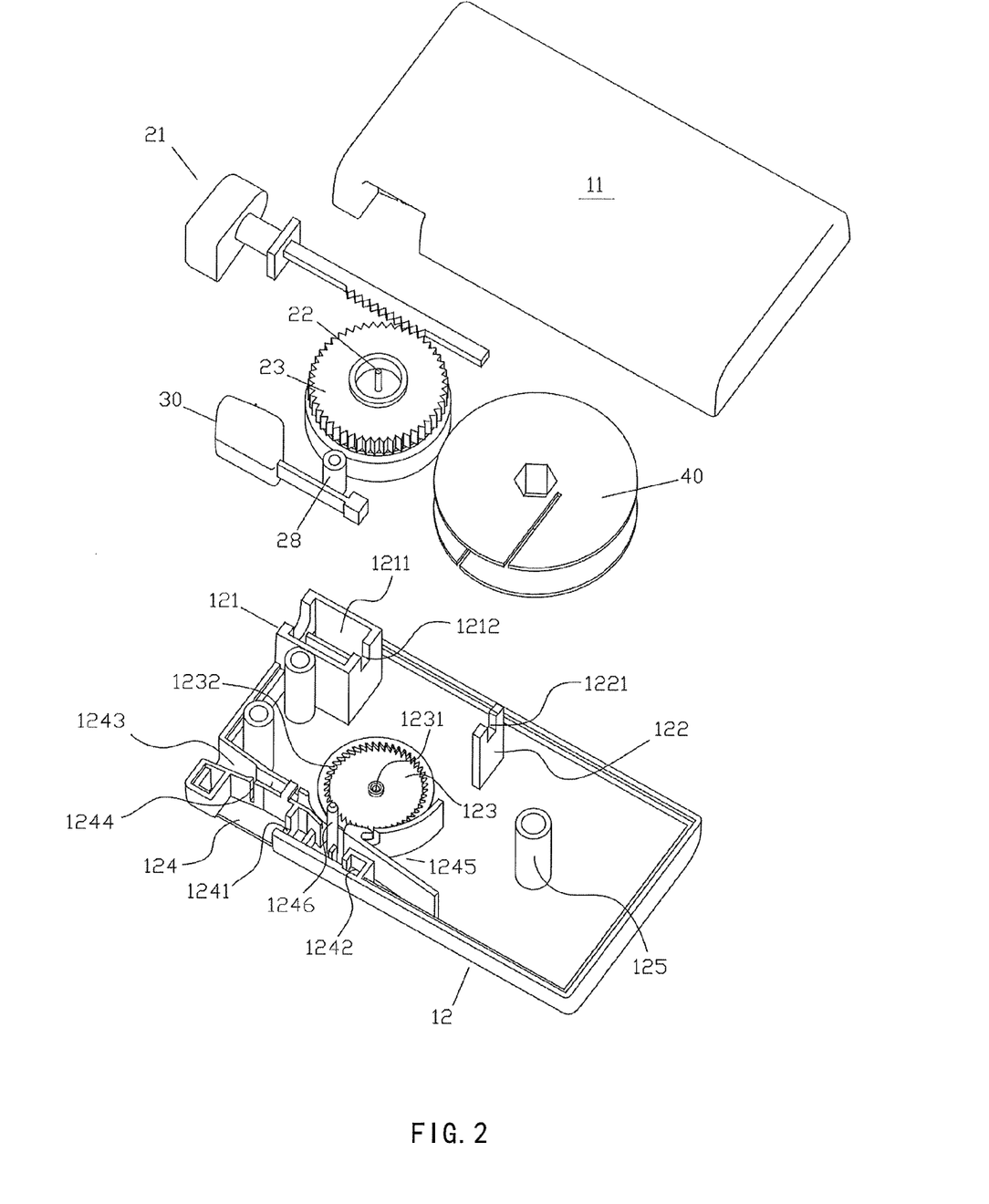
FIG. 2 is a further exploded view of the strip-shaped storing and transferring device of FIG. 1.

Referring to the FIG. 2, the upper case 11 and the lower case 12 are matched and can be engaged together, thereby, only the lower case 12 is taken for example for detailed description. The lower case 12 includes a rectangle portion 121, a bulge portion 122, a position portion 123 for fixing a main axle 22 therein, a recess groove 124 for fixing the wire cutting mechanism 30, and a position pole 125 for limiting the rotation of the bobbin winder 40.

The rectangle portion 121 close to an edge of a corner of the lower case 12 includes a recess portion 1211 and a recess opening 1221. The recess portion 1211 is capable of clamping a resisting portion 213 of a pressure pole 21 to move up and down in the rectangle portion 121. The recess opening 1221 is defined opposite to an outlet 1212 of the recess portion 1211 and the top of the bulge portion 122. The and looks like a line formed by two points. Thus mechanism limits a main pole 212 only to move up and down within the case 10 when the upper case 11 and the lower case 12 are engaged together.

The position portion 123 is disposed between the upper case 11 and the lower case 12 and closes to the recess groove 124, and includes a position hole 1231 and a stopping portion 262 defined on the back of the anti-reverse-rotation device 26.

The recess groove 124 is defined on the edge of the corner opposite to the rectangle portion 121. The recess groove 124 defines a clamping portion 1241 and a fixing portion 1242 along a long sidewall. The recess groove 124, the clamping portion 1241, and the fixing portion 1242 are a mating structure of the wire cutting mechanism 30. The recess groove 124 has a common wall with an outgoing line groove 1243. The middle portion of the common wall defines a crack 1244 that communicates with the recess groove 124 and the outgoing line groove 1243. The outgoing line groove 1243 also communicates with an incoming line groove 1245. A position pole 1246 for fixing a subordinate rolling wheel 28 is defined on a side between the clamping portion 1241 and the fixing portion 1242 and close to the side where the clamping portion defined.

Figure 3:
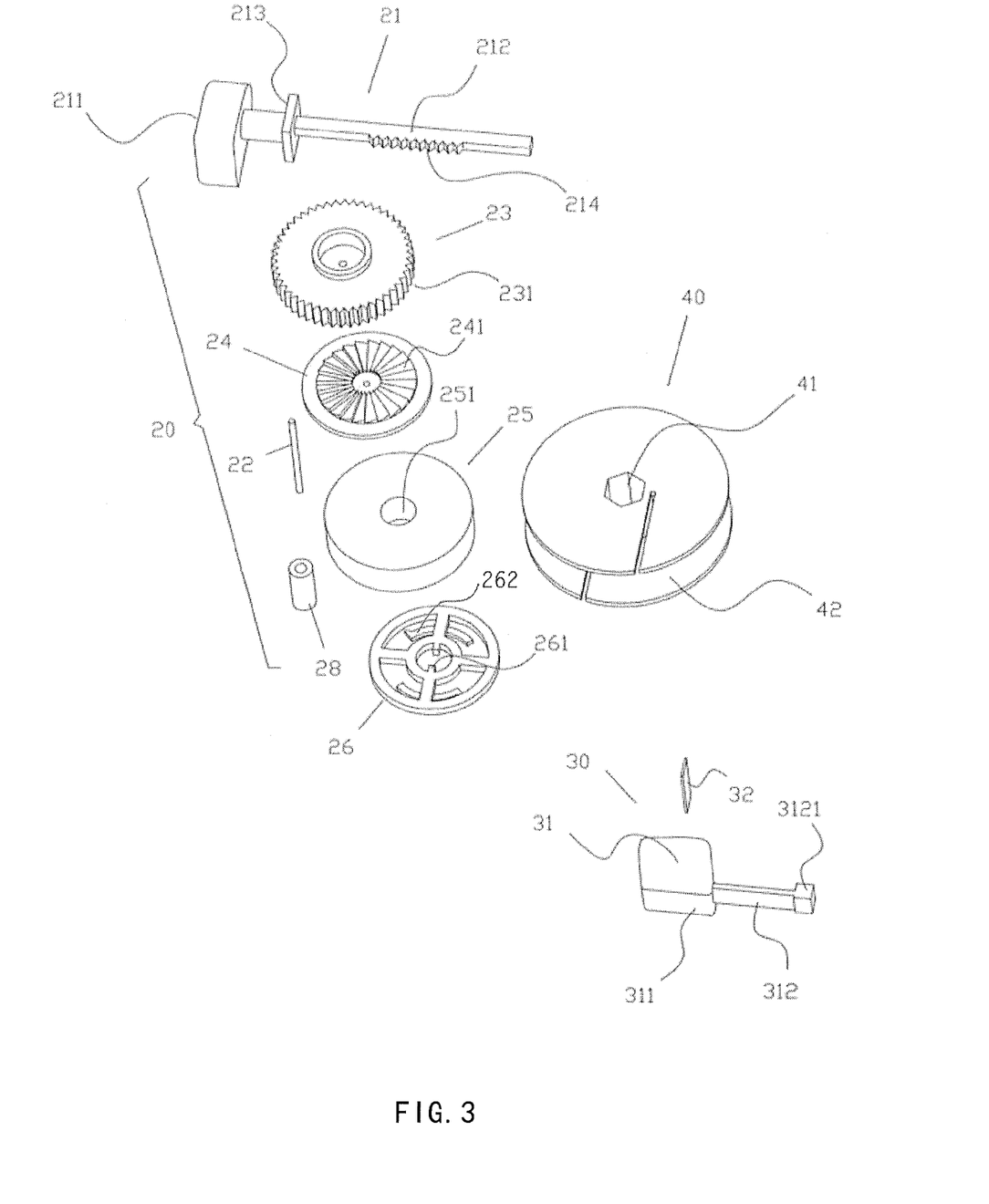
FIG. 3 is an exploded views of a driving mechanism, a wire cutting mechanism, and a bobbin winder of FIG. 1.
Figure 4:
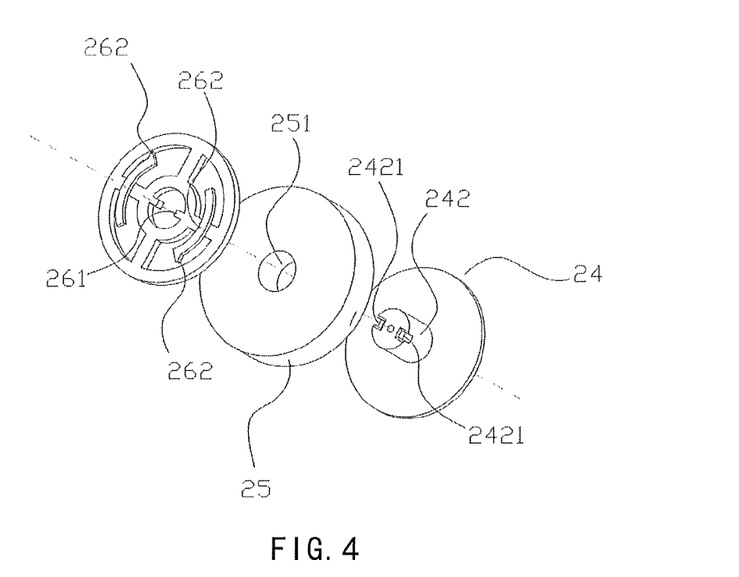
FIG. 4 is another perspective view of a rotating wheel, a main rolling wheel, and an anti-reverse-rotation device of FIG. 3.
Figure 5:
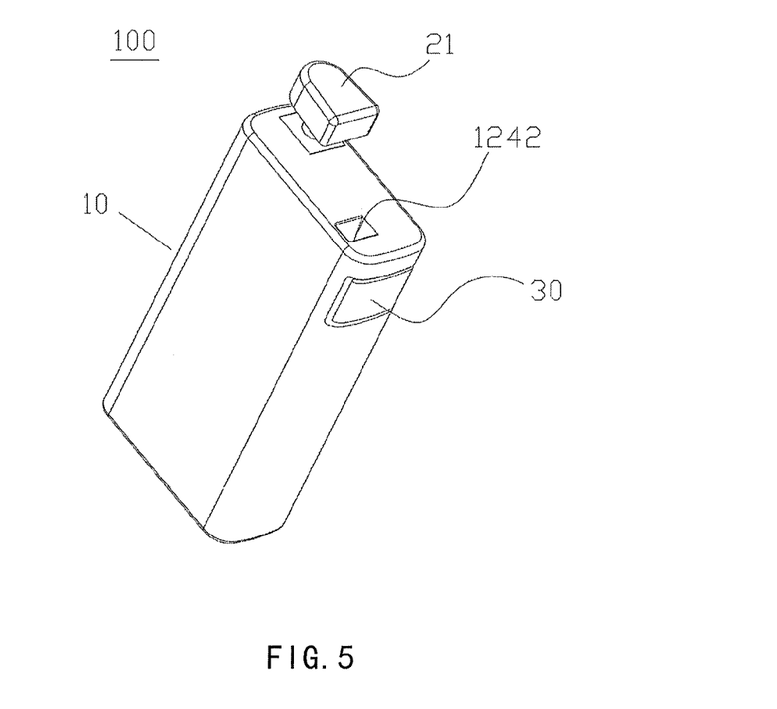
FIG. 5 is an assemble perspective view of the strip-shaped storing and transferring device of FIG. 1.

Referring to FIG. 3 and FIG. 4, the driving mechanism 20 includes a pressure pole 21, a main gear 23, a rotating wheel 24, a main rolling wheel 25, and an anti-reverse-rotation device 26 resisted by a second elastic element 29 (for example, a spring), wherein the main gear 23, the rotating wheel 24, and the main rolling wheel 25 are strung by a main axle 22.

The pressure pole 21 includes a main pole portion 212 connected by a pressure cap 211. The main pole portion 212 defines a resisting portion 213 close to the pressure cap 211 for matching with a first elastic element 27, and further defines a first sawtooth portion 214 on one side of the middle section of the main pole portion for driving the main gear 23.

The main gear 23 further defines a second sawtooth portion 231 engaging with the first sawtooth portion 214 on a periphery thereof, and a third sawtooth portion (not shown) on the bottom surface thereof. The third sawtooth portion engages with the fourth sawtooth portion 241 defined on the surface of the rotating wheel 24.

The main rolling wheel 25 rotates simultaneously with a rotation axle 242 which fixed on the bottom of the rotation wheel 24, thereby, the wire (not shown) on the bobbin winder 40 clamped between the main rolling wheel 25 and the subordinate rolling wheel 28 is pulled from the incoming line groove 1245 to the outgoing line groove 1243.

The anti-reverse-rotation device 26 clamping the main rolling wheel 25 with the rotation wheel 24 includes bulge points 261 being capable of engaging in concave points 2421 on the rotation wheel 242, and stopping portions 262 matching with inverse teeth 1232 on the position portion 123. The inverse teeth 1232 and the stopping portions 262 enable the main rolling wheel 25 only rotate in clockwise and cannot rotate inversely under the function of the second elastic element 29.

Referring to FIG. 1 and FIG. 3, the wire cutting mechanism 30 fixed by the mating structure of the case 10 includes a cutter shelf 31 and cutters 32. The cutter shelf 31 includes a button 311 and a straight pole 312. The straight pole 312 has a holding portion 3121 on the symmetrical end of the button 311. In the wire cutting mechanism 30, the button 311 of the cutter shelf 31 is placed in the recess groove 124 and is tightly fixed with the clamping portion 1241 and the fixing portion 1242 of the lower case 12 by the straight pole 312 and the holding portion 3121 thereof. The cutter 32 is fixed on the inner side of the button 311. During assembling, the button 311 is placed in the recess groove 124, when the button 311 is pressed, the cutter 32 passes the crack 1244 to cut off the wire passing through the outgoing line groove 1243.

Referring to FIGS. 1 and 2, the bobbin winder 40 positioned by the position pole 125 of the case 10 includes a center hole 41 and a bobbin slot 42.

Based on the above description, the invention that the strip-shaped wire-shaped materials storing and dispensing device is realized.

An operating process of the device provided in the invention will be described below.

When the pressure pole 21 is pressed, the first sawtooth portion 214 moves along the pressing direction. When the pressing operation is stopped, the first elastic element 27 return to an original position under the elastic force generated by the first elastic element 27.

After mechanical coupling, the first sawtooth portion of the pressure pole 21 pushes the main gear 23 to rotate. The main gear 23 rotates with a constant angle.

When rotating in a forward direction under the pressure of the pressure cap 211, the rotation of the main gear 23 drives the rotating wheel 24 to rotate simultaneously. When rotating in a reverse direction, because the fourth sawtooth portion 241 of the rotation wheel 24 engages with the third sawtooth portion of the main gear 23 in a single direction, under the function of the stopping portion 262 of the anti-reverse-rotation device 26 and the reverse teeth 1232, the main gear 23 makes the rotating wheel 24 can not move and follow the reverse rotation of the main gear 23. When the pressure pole 21 is pressed one time, the rotating wheel 24 clockwise rotates a constant angle with the main rolling wheel 25 clamped by the anti-reverse-rotation device 26.

When the main gear 23 rotates in a reverse direction, the stopping portion is blocked on the reverse teeth 1232 of the lower case 12, simultaneously combining the elastic function of the second elastic element 29, the reverse rotation of the rotating wheel 24 and the rolling wheel 25 are prevented.

The wire is clamped between the main rolling wheel 25 and the subordinate rolling wheel 28, the subordinate rolling wheel 28 is driven by the main rolling wheel 25, thereby, the wire in the bobbin winder 40 is pulled to the predefined in the incoming line groove 1245 by the main rolling wheel 25 and the subordinate rolling wheel 28, and then the wire is output from the outgoing line groove 1243. Because the main rolling wheel 25 rotates at a constant angle, the length that the wire is pulled is also a constant length, thereby, the wire can be cut off precisely, thus reduce the waste of wire.

In the embodiment of the present invention, the incoming line groove 1245 and the outgoing line groove 1243 both are trumpet shaped to ensure the wire loaded smoothly.

When the wire is pulled to the position of the outgoing line groove 1243, pressing the cutter shelf 31, the cutter 32 fixed together with the cutter shelf 31 cuts the output wire, thus, the operation process of the present invention is completed.

Figure 6:
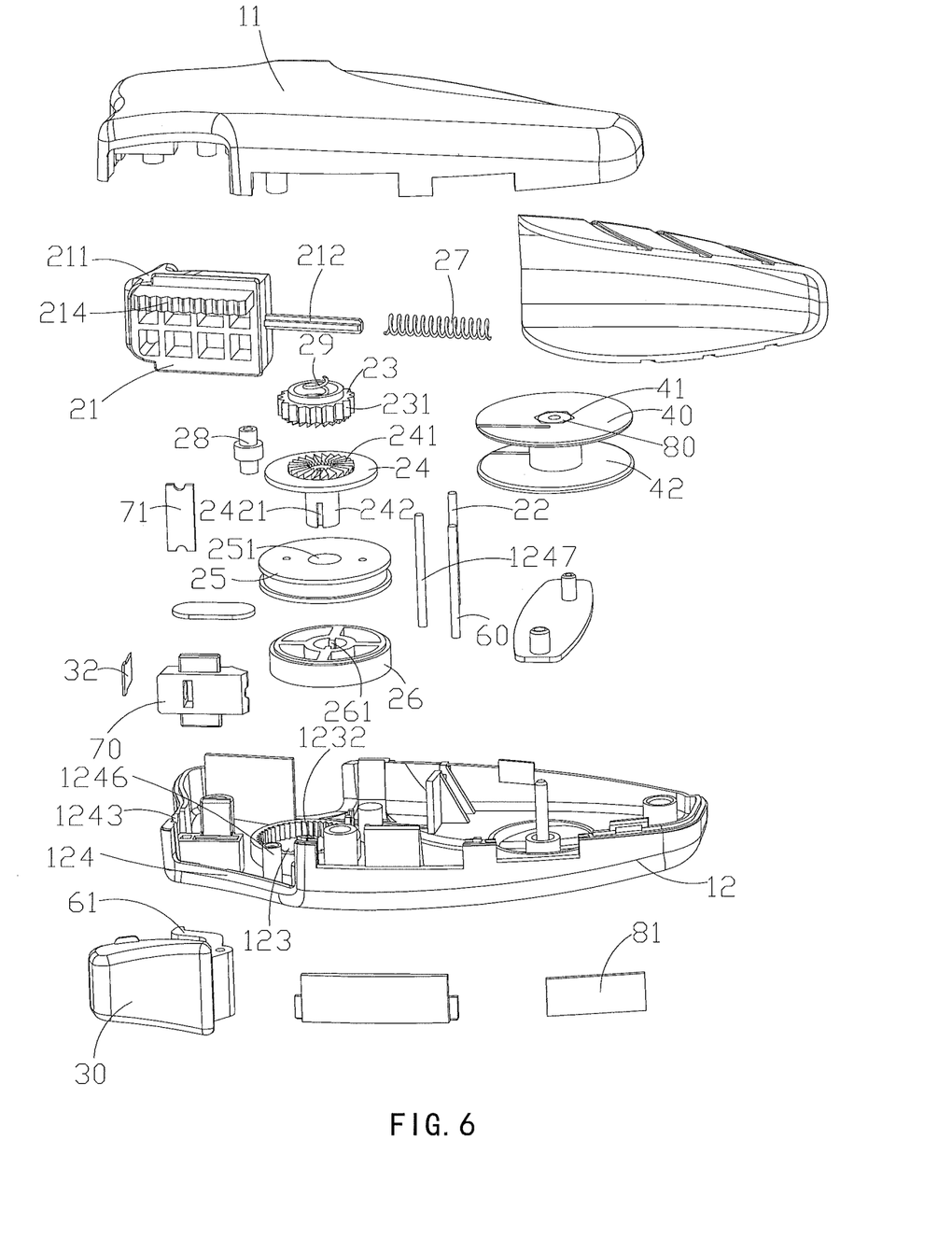
FIG. 6 is an exploded view of the strip-shaped storing and transferring device in accordance with a second preferred embodiment of the present invention.
Figure 7:
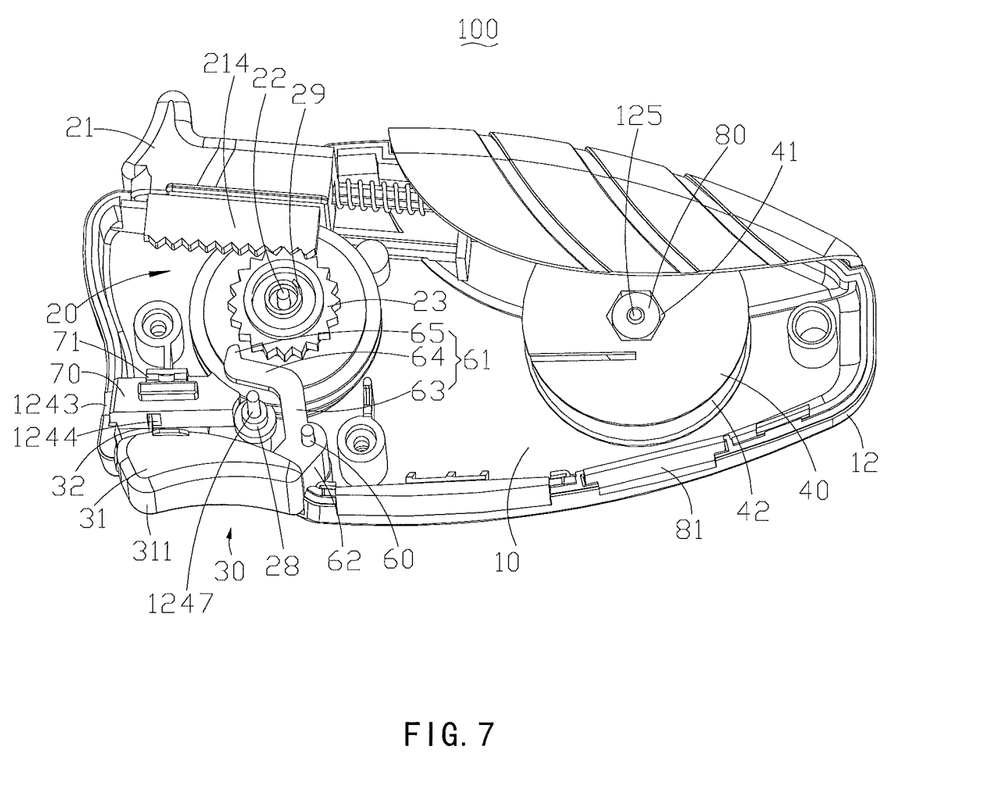
FIG. 7 shows a partial structure of the strip-shaped storing and transferring device of FIG. 6 after being assembled, wherein, a clamping arm of a cutter shelf does not clamp to the main gear.
Figure 8:
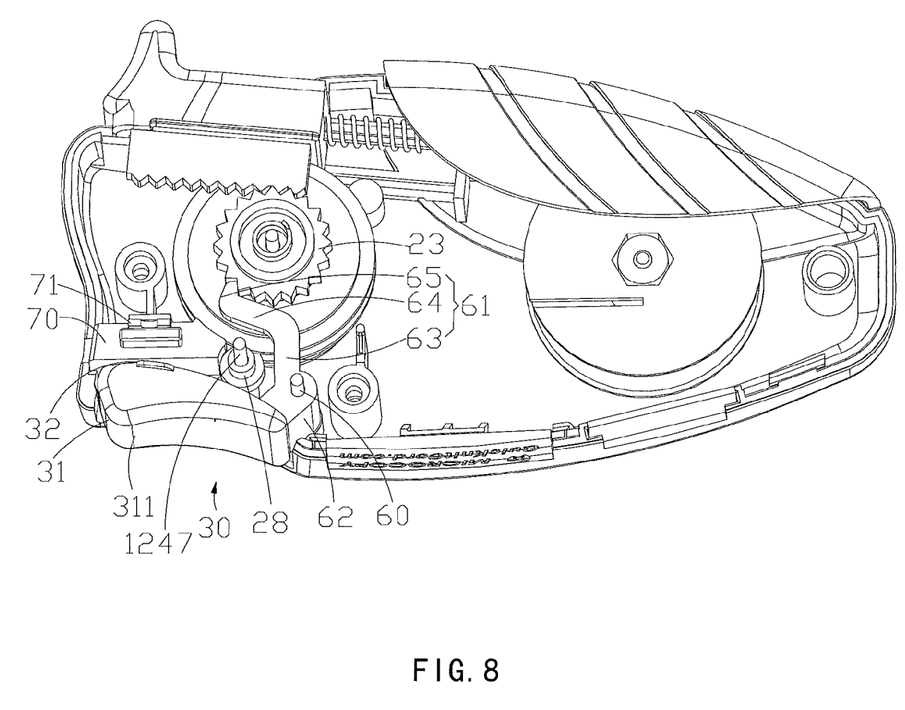
FIG. 8 shows a partial structure of the strip-shaped storing and transferring device of FIG. 6 after being assembled, wherein, the clamping arm of the cutter shelf clamps to the main gear.

Referring to FIG. 6 to FIG. 8, the second preferred embodiment of the present invention provides a strip-shaped wire-shaped materials storing and dispensing device 100 similar to the strip-shaped wire-shaped materials storing and dispensing device 100 provided in the first preferred embodiment. Herein, only more important structure of the strip-shaped wire-shaped materials storing and dispensing device 100 provided in the second preferred embodiment is described.

The strip-shaped wire-shaped materials referred herein includes line-shaped strip, wire and cord. The device 100 includes a driving mechanism 20 covered by a case 10, a wire cutting mechanism 30, and a bobbin winder 40.

The case 10 includes an upper case 11 and a lower case 12.

Referring to the FIG. 2, the upper case 11 and the lower case 12 are matched and can be bucked together, thereby, only the lower case 12 is taken for example for detailed description. The lower case 12 includes a position portion 123 for fixing a main axle 22, a recess groove 124 for fixing the wire cutting mechanism 30, and a position pole 125 for limiting the rotation of the bobbin winder 40. A pressure pole 21 is fixed on the upper left corner of the lower case 12, and the first sawtooth portion 214 is limited only to move up and down within the case 10 when the upper case 11 and the lower case 12 are engaged together.

The position portion 123 between the upper case 11 and the lower case 12 and close the recess groove 124 includes a position hole (not shown) for fixing the main axle 22.

The recess groove 124 is defined on the edge of the lower-right corner of the lower case 12. One side of the lower case 12 defines the outgoing line groove 1243.

The position pole 1246 for fixing the subordinate rolling wheel 28 protrudes from the lower case 12. The subordinate rolling wheel 28 is fixed on an axel 1247 of the position pole 1246.

The driving mechanism 20 includes the pressure pole 21, a main gear 23, a rotating wheel 24, a main rolling wheel 25, and a anti-reverse-rotation device 26, wherein the main gear 23, the rotating wheel 24, and the main rolling wheel 25 are strung by a main axle 22 and resisted by the second elastic element 29.

The pressure pole 21 includes the pressure cap 211, the first sawtooth portion 214 connected with the pressure cap 211, and the main pole portion 212 for surrounding by the first elastic element 27.

The main gear 23 includes further defines the second sawtooth portion 231 engaging with the first sawtooth portion 214 on a periphery thereof, and the third sawtooth portion (not shown) on the bottom surface thereof. The third sawtooth portion engages with the fourth sawtooth portion 241 defined on the surface of the rotating wheel 24.

The subordinate rolling wheel 28 is defined adjacent to the main rolling wheel 25. The main rolling wheel 25 rotates simultaneously with a rotation axle 242 which fixed on the bottom of the rotation wheel 24, thereby, the wire (not shown) on the bobbin winder 40 clamped between the main rolling wheel 25 and the subordinate rolling wheel 28 is pulled from the incoming line groove 1245 to the outgoing line groove 1243.

The anti-reverse-rotation device 26 clamping the main rolling wheel 25 with the rotation wheel 24 includes bulge points 261 being capable of engaging in concave points 2421 on the rotation wheel 242, and the stopping portions (alike the reference number 262 in FIG. 3 of the first preferred embodiment) matching with inverse teeth 1232. The inverse teeth 1232 and the stopping portions 262 enable the main rolling wheel 25 only rotate in clockwise and cannot rotate inversely under the function of the second elastic element 29.

The wire cutting mechanism 30 fixed by the complementary construction of the case 10 includes a cutter shelf 31 and cutters 32.

The below case 12 defines a rotation shaft 60. The cutter shelf 31 includes the button 311 and a clamping arm 61 bending and extending towards the main axle 22 from one end of the button 311, the clamping arm 61 is capable of clamping to the second sawtooth portion 231 of the main gear 23 to limit the rotation of the main gear 23. A pivot connection portion 62 is disposed between the clamping arm 61 and the end of the button 311. The rotation shaft 60 passes through the pivot connection portion 62 and enables the pivot connection portion 62 rotate around the rotation shaft 60. The clamping arm 61 includes a first straight section 63 connected to the pivot connection portion 62, a second straight section 64 connected to a free end of the first straight section 63, and a hook 65 defined on one end of the second straight section 64.

The first straight section 63 and the second straight section 64 together form a bend shape. The first straight section 63 and the second straight section 64 encloses an avoiding space (not shown). The subordinate rolling wheel 28 seats in the avoiding space, namely, the clamping arm 61 avoids the subordinate rolling wheel 28 by the bending structure formed by the first straight section 63 and the second straight section 64 to avoid the interference. The hook 65 is capable of hooking the second sawtooth portion 231 of the main gear 23.

The button 311 of the cutter shelf 31 of the wire cutting mechanism 30 is placed in the recess groove 124. The cutter 32 is fixed on the inner side of the button 311. During assembling, the button 311 is placed in the recess groove 124, when the button 311 is pressed, the cutter 32 passes the crack 1244 to cut off the wire passing through the outgoing line groove 1243.

In the embodiment, the crack 1244 is defined on a block 70. The block 70 is fixed between the upper case 11 and the lower case 12 and corresponds to the outgoing line groove 1243. The back of the block 70 defines a metal board 71. The cutter 32 cuts the strip-shaped wire from the front of the block 70 by coordinating with the metal board 71.

When the button 311 is pressed, the cutter shelf 31 rotates around the rotation shaft 60, the cutter 32 cuts the strip-shaped wire from the front of the block 70 by coordinating with the metal board 71, simultaneously, the hook 65 hooks the second sawtooth portion 231 of the main gear 23 to limit the main gear 23, thus avoids the pressure pole 21 being unintendedly operated to dispense the wire, thereby causing block of the wire.

Relative to the cooperation of the cutter 32 and a plastic wall, the cooperation of the cutter 32 and the metal board 71 for cutting the wire is cleaner and also cannot damage the metal board 71 when the button 311 is pressed overexerting.

When the button 311 is released, the button 311 is recovered to the original state, the cutter shelter 31 rotates reversely around the rotation shaft 60, the cutter 32 leaves from the metal board, simultaneously, the hook 65 breaks away from the second sawtooth portion 231 of the main gear 23, thereby the wire is cut at one time.

The positioned by the position pole 125 of the case 10 includes a center hole 41 and a bobbin slot 42. The position hole 125 is putted into the center hole 41. The bobbin winder 40 includes an elastic pole 80 surrounds the position pole 125. The elastic pole 80 is inside the center hole 41, for specifically, the elastic pole 80 is clamped between the inner surface of the center hole 41 and the position pole 125 to increase the rotation resistance of the bobbin winder 40, and balance the driving pull force of the wire to make input of the wire is more stable, and can not generate unnecessary wire input due to the inertia of the bobbin winder 40, thus avoids the wire is blocked in the case 10.

The elastic pole 80 is barrel-shaped and is made of elastic wire.

In the embodiment, one side of the case 10 defines a watch window 81. The watch window 81 corresponds to the bobbin winder 40 and is configured for user conveniently watching the remainder of the wire.

An operating process of device provided in the invention will be described below.

When the pressure pole 21 is pressed, the first sawtooth portion 214 moves along the pressing direction. When the pressing operation is stopped, the first elastic element 27 returns to the original position under the elastic force generated by the first elastic element 27.

After mechanical coupling, the first sawtooth portion of the pressure pole 21 pushes the main gear 23 to rotate. The main gear 23 rotates with a constant angle.

When rotating in a forward direction under the pressure of the pressure cap 211, the rotation of the main gear 23 drives the rotating wheel 24 to rotate simultaneously. When rotating in a reverse direction, because the fourth sawtooth portion 241 of the rotation wheel 24 engages with the third sawtooth portion of the main gear 23 in a single direction, under the function of the stopping portion 262 of the anti-reverse-rotation device 26 and the reverse teeth 1232, the main gear 23 makes the rotating wheel 24 can not move and follow the reverse rotation of the main gear 23. When the pressure pole 21 is pressed each time, the rotating wheel 24 clockwise rotates a constant angle with the main rolling wheel 25 clamped by the anti-reverse-rotation device 26.

When the main gear 23 rotates in a reverse direction, the stopping portion is blocked on the reverse teeth 1232 of the lower case 12, simultaneously combining the elastic function of the second elastic element 29, the reverse rotation of the rotating wheel 24 and the rolling wheel 25 are prevented.

The wire is clamped between the main rolling wheel 25 and the subordinate rolling wheel 28, the subordinate rolling wheel 28 is driven by the main rolling wheel 25, thereby, the wire in the bobbin winder 40 is pulled to the predefined in the incoming line groove 1245 by the main rolling wheel 25 and the subordinate rolling wheel 28, and then the wire is output from the outgoing line groove 1243. Because the main rolling wheel 25 rotates at a constant angle, the length that the wire is pulled is also a constant length, thereby, the wire can be cut off precisely, thus reduce the waste of wire.

In the embodiment of the present invention, the incoming line groove 1245 and the outgoing line groove 1243 both are trumpet shaped to ensure the wire loaded smoothly.

When the wire is pulled to the position of the incoming line groove 1245, pressing the cutter shelf 31, the cutter 32 fixed together with the cutter shelf 31 cuts the output wire, thus, the operation process of the present invention is completed.

The above described strip-shaped wire-shaped materials storing and dispensing device 100 is just the preferred embodiment of the present invention, and is not intend to limit the present invention. The scope of the invention is indicated by the appended claims rather than by the foregoing description; and all changes which come within the meaning and range of equivalency of the claims are intended to be embraced therein.

What is claimed is:

1. A line-shaped wire storing and transferring device, comprising:
a driving mechanism covered by a case, a wire cutting mechanism, and a bobbin winder, wherein:
the case comprises an upper case and a lower case, the upper case and the lower case are matched and capable of engaging together, the case comprises a rectangle portion, a bulge portion, a position portion, a position pole, and an incoming line groove and an outgoing line groove communicate with a recess groove,
the wire cutting mechanism comprises a cutter shelf and a cutter,
the bobbin winder comprises a center hole and a bobbin slot,
the driving mechanism includes a pressure pole, a main gear, a rotating wheel, a main rolling wheel, and an anti-reverse-rotation device resisted by a second elastic element, wherein the main gear, the rotating wheel, and the main rolling wheel are strung by a main axle,
the pressure pole includes a main pole portion connected by a pressure cap; the main pole portion defines a resisting portion close to the pressure cap for matching with a first elastic element, and further defines a first sawtooth portion on one side of the middle section of the main pole portion for driving the main gear,
the main gear further defines a second sawtooth portion engaging with the first sawtooth portion on a periphery thereof, and a third sawtooth portion on the bottom surface thereof,
the main rolling wheel rotates simultaneously with a rotation axle which is fixed on the bottom of the rotation wheel, the wire on the bobbin winder clamped between the main rolling wheel and a subordinate rolling wheel is pulled from the incoming line groove to the outgoing line groove,
the anti-reverse-rotation device clamping the main rolling wheel with the rotation wheel includes bulge points capable of engaging in concave points on the rotation wheel, and stopping portions matching with inverse teeth on the position portion, and
the inverse teeth and the stopping portions enable the main rolling wheel to only rotate clockwise and cannot rotate inversely under the function of the second elastic element.

2. The line-shaped wire storing and transferring device as claimed in claim 1, wherein the rectangle portion comprises a recess portion being capable of sticking a resisting portion of the pressure pole and a first elastic element, a recess opening is arranged opposite to an outlet of the recess portion and the top of the bulge portion.

3. The line-shaped wire storing and transferring device as claimed in claim 1, wherein the position portion comprises a position hole and reverse teeth.

4. The line-shaped wire storing and transferring device as claimed in claim 1, the recess groove defines a clamping portion along a longer inner sidewall and a fixing portion extending from the clamping portion.

5. The line-shaped wire storing and transferring device as claimed in claim 1, wherein the recess groove and the outgoing line groove are disposed on a common wall, the common wall defines a crack that communicates with the recess groove and the outgoing line groove, and the outgoing line groove further communicates with the incoming line groove.

6. The line-shaped wire storing and transferring device as claimed in claim 1, wherein the cutter shelf comprises a button and a holding portion, the cutters are fixed on an inner side of the button, and the button is placed in the recess groove.

7. The line-shaped wire storing and transferring device as claimed in claim 1, wherein the inlet of the incoming line groove and the outlet of the outgoing line groove are inverted awl shaped, the cutting position of the cutter is disposed on the top of the inverted awl shaped outlet of the outgoing line groove.

8. The line-shaped wire storing and transferring device as claimed in claim 1, further comprises an elastic pole surrounds the position pole , the position pole passes through the center hole of the bobbin winder and the elastic pole is clamped between the inner surface of the center hole and the position pole.

9. The line-shaped wire storing and transferring device as claimed in claim 1, wherein the side of the case defines a watch window, the watch window corresponds to the bobbin winder.

10. The line-shaped wire storing and transferring device as claimed in claim 1, further comprising a block fixed between the upper case and the lower case, wherein the block corresponds to the outgoing line groove, the back of the block defines a metal board, the cutter cuts the strip-shaped wire from the front of the block by coordinating with the metal board.

11. The line-shaped wire storing and transferring device as claimed in claim 1, wherein the cutter shelf comprises a button and a clamping arm bending and extending towards the main axle from one end of the button, and the clamping arm is capable of clamping to the main gear to limit the rotation of the main gear.

12. The line-shaped wire storing and transferring device as claimed in claim 11, wherein a pivot connection portion is arranged between the clamping arm and the end of the button, the clamping arm comprises a first straight section connected to the pivot connection portion, a second straight section connected to a free end of the first straight section, and a hook defined on an end of the second straight section, and the hook is capable of hooking the main gear.

* * * * *